United States Patent [19]
Dix

[11] Patent Number: 5,435,330
[45] Date of Patent: Jul. 25, 1995

[54] DENTAL FLOSS DEVICE

[76] Inventor: Sean Dix, 145 E. 15th St., Apt. #12A, New York, N.Y. 10003

[21] Appl. No.: 223,168
[22] Filed: Apr. 5, 1994
[51] Int. Cl.$^6$ ............................................. A61C 15/00
[52] U.S. Cl. .................................................... 132/323
[58] Field of Search ............... 132/323, 324, 325, 326, 132/327

[56] References Cited

U.S. PATENT DOCUMENTS

| 664,014 | 12/1890 | Coryell | 132/323 |
|---|---|---|---|
| 788,947 | 5/1905 | Roth | 132/323 |
| 1,559,320 | 10/1925 | Hirsch . | |
| 2,162,240 | 6/1939 | Boldusoff | 132/327 |
| 2,180,522 | 11/1939 | Henne | 132/323 |
| 3,474,799 | 10/1969 | Cappello | 132/323 |
| 4,006,750 | 2/1977 | Chodorow . | |
| 4,013,085 | 3/1977 | Wright | 132/323 |
| 4,016,892 | 4/1977 | Chodorow . | |
| 4,034,770 | 7/1977 | Trecker . | |
| 4,050,470 | 9/1977 | Miller . | |
| 4,162,687 | 7/1979 | Lorch | 132/323 |
| 4,403,625 | 9/1983 | Sanders . | |
| 4,638,824 | 1/1987 | De La Hoz . | |
| 4,655,233 | 4/1987 | Laughlin | 132/323 |
| 4,729,392 | 3/1988 | Tenny | 132/323 |
| 4,807,651 | 2/1989 | Naydich . | |
| 4,807,752 | 2/1989 | Chodorow . | |
| 4,926,820 | 5/1990 | Wearn . | |
| 4,941,488 | 7/1990 | Marxer et al. | 132/323 |
| 5,222,510 | 6/1993 | Zuehlsdorf . | |
| 5,224,501 | 7/1993 | McKenzie . | |

*Primary Examiner*—Nicholas D. Lucchesi

[57] ABSTRACT

The invention provides for a dental floss device comprising two ring portions and a floss portion held therebetween, whereby the ring portions are placed on a finger of each hand of a user. The ring portions are specially adapted to receive and removingly retain a specially formed segment of floss, which segment of floss can be removed from the rings and discarded, while the ring portions are fitted with a new segment of floss and reused. The floss portion has locking elements on each end which engage with a mating receiving portion on each ring portion.

11 Claims, 1 Drawing Sheet

DENTAL FLOSS DEVICE

The present invention relates to a dental floss device. More particularly, the present invention relates to a device comprising two ring elements adapted to receive and retain a segment of dental floss designed to engage a retaining means on the ring elements, which device can be easily manipulated within the mouth for improved flossing.

BACKGROUND OF THE INVENTION

Standard dental floss consists of a thin string or ribbon, usually of plastic or the like, which is stored within a container. Typically, the container acts as a dispensing device, and has a cutting element thereon for cutting a piece of dispensed floss at a desired length. This simple segment of floss is then wound at both ends about a finger on each hand, and held in place by an adjacent finger. Accordingly, when dental floss is used in this manner, it requires that two fingers on each hand be placed within the mouth to achieve the desired flossing action. Furthermore, when any type of turning or rotational motion is required to reach the back teeth, the problem of having four fingers inside the mouth becomes amplified.

The advantage of providing a dental floss device utilizing finger loops was taught by Trecker in U.S. Pat. No. 4,034,770. The use of finger loops having a segment of dental floss suspended therebetween allows for easier manipulation within the mouth, as only one finger on each is needed, and the floss is securely retained by the fingers without slippage. The Trecker device utilizes the standard floss roll container as described above, except that the floss is tied into finger loops at set intervals. The floss is pulled from the container and cut at a length so as to provide two finger loops formed from floss, with a segment of floss suspended therebetween. While this device is an improvement over the standard flossing device, it suffers from the disadvantage that the finger loops formed of tied-off floss ribbon will have the tendency to cause discomfort to the finger when tension is applied during flossing operation. In addition, it is likely that the roll of floss having the tied-off loops thereon would tend to become tangled within the container, thereby resulting in inoperativeness of the device.

Some of the disadvantages of the Trecker device are addressed in U.S. Pat. No. 4,638,824 to De La Hoz, which teaches two rigid finger rings adapted to removably retain a standard segment of dental floss therebetween. The finger rings have a retaining portion extending laterally from the ring portion, the retaining portion having three cut out prongs extending slightly upwardly, which alternate with respect to the direction in which they open. The end portion of a cut segment of floss is then wound around the three prongs to retain the floss. The De La Hoz device suffers from a disadvantage in that the standard floss segment will have a tendency to either pull out of the retaining prongs or to be cut at the point of retention as a result of the strong force exerted during flossing operation. In addition, the fact that the retaining prongs extend upwardly from the flat surface of the retaining portion leaves open the possibility that the prongs could cause injury to the inside of the mouth. Furthermore, the manipulation of the end of the floss segment to wind it around the three prongs may be difficult for those persons lacking the requisite dexterity.

It is therefore an object of the present invention to provide a dental floss device which requires a minimal degree of finger protrusion into the mouth, but which provides the necessary leverage to achieve proper flossing action, and which furthermore allows for easy rotation of the fingers within the mouth to reach the back teeth.

It is a further object of the present invention to provide a dental floss device which avoids economic and environmental waste by providing a reusable floss retaining portion which is used in conjunction with a floss portion replaced after each use.

It is a still further object of the present invention to provide a dental floss device having finger rings which are comfortably worn on the fingers, and which do not have upwardly extending protrusions which may cause injury to the mouth.

It is another object of the present invention to provide retaining means on the finger rings which act in conjunction with specially adapted floss segments for simple, secure, one-step engagement between the floss segment and the finger rings.

SUMMARY OF THE INVENTION

Accordingly, the present invention provides for a dental floss device comprising two ring portions and a floss portion held therebetween, whereby the ring portions are placed on a finger of each hand of a user, resulting in an improved flossing mechanism which requires that only two fingers be placed within the mouth. Additionally, the device of the invention provides for increased leverage and mobility within the mouth, resulting in ease of flossing and improved results.

The ring portions should be sized to fit over and be retained upon a finger of the user, and the floss portion should be of a size which will allow for full extension between two fingers within the mouth, generally less than about four inches. The ring portions and floss portions may be integral with one another so as to form a unified device which will be wholly discarded after each use. Preferably, the ring portions are specially adapted to receive and removingly retain a segment of floss, which segment of floss can be removed from the rings and discarded, whilst the ring portions are fitted with a new segment of floss and reused. Even more preferable is an embodiment of the device in which the ring portions are adapted to receive a specially formed floss portion, which floss portion has locking means at either end which engage with a mating receiving means on each ring portion. Again, the specially formed floss portion can be removed from the ring portions and discarded after each use, while the ring portions may be used repeatedly.

BRIEF DESCRIPTION OF THE DRAWINGS

The invention will now be described with respect to the following drawings.

DETAILED DESCRIPTION OF THE INVENTION

Figure 1:
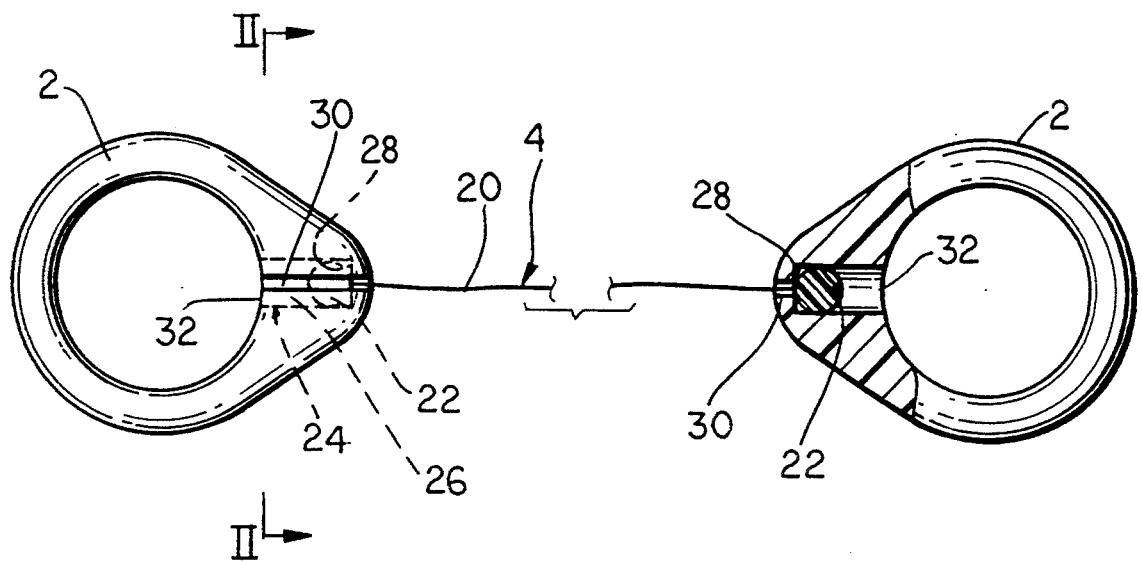
FIG. 1 is a top view of the invention, showing one ring portion schematically, and the other ring portion in partial cross-section taken along line I—I of FIG. 2.
Figure 2:
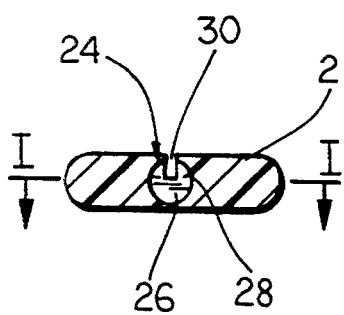
FIG. 2 is a cross-sectional view of a ring portion of the invention, taken along line II—II of FIG. 1.

As shown in FIGS. 1 and 2, the invention comprises two separate ring portions 2 and a floss portion 4 held therebetween. The ring portions 2, which may be toroidal or flat, are generally sized to fit around the finger of a human user. Ring portions of varying inside diameters may be provided to allow the user to choose the appropriate size. In addition, the ring portions may be made of resilient material to allow for different finger sizes, and also to provide added comfort to the fingers during flossing activity by relieving excess pressure upon the fingers. Furthermore, the inside diameter of the ring portions should be relatively smooth and free of protuberances, so as to protect and provide comfort for the finger. The floss portion 4 comprises a standard segment of dental floss, usually a plastic ribbon for insertion between adjacent teeth. During use, one ring portion 2 is placed securely about and retained upon a finger on each hand. The user then manipulates the segment of floss within the mouth by simply moving the two engaged fingers.

The floss portion 4 comprises a segment of floss 20 having at either end locking means 22 which are engageable with retaining means 24 on each ring portion 2. The locking means 22 are comprised of an enlarged portion at the end of the segment of floss 20, and may be in the form of a bead as shown, or other shape capable of locking engagement such as a perpendicular member forming a T-shaped locking means. The retaining means 24 are formed to receive and retain the locking means 22 to thereby hold the floss portion 4 securely between the two ring portions 2.

The retaining means 24 may be a hollow elongate member as shown, and has a first opening 26 to allow for insertion of the locking means 22. While the first opening 26 is shown in the figures as opening toward the inside of the ring portion, it may also be effectively situated so as to open in any direction. The first opening 26 communicates with an inside wall of the retaining means, which inside wall acts as an abutting end 28. The abutting end 28 should be an inside wall which faces toward the center of the ring portion 2, so as to forcibly act against the locking means 22 in the direction toward the center of the ring portion when the locking means 22 is pulled away from center via the segment of floss 20 during flossing activity.

A second opening 30 to the inside of the retaining means 24 is a slit-like opening which extends from the edge 32 of the first opening 26 and runs along the retaining means 24. The second opening 30 should be large enough to permit the segment of floss 20 of the floss portion 4 to pass therethrough, but must be small enough to prevent the passage therethrough of the locking means 22. The locking means 22 fixably attached to a segment of floss is inserted into the first opening 26 of the retaining means 24 until the locking means comes to rest against the abutting end 28. The segment of floss extending from the locking means 22 is allowed to protrude from the retaining means 24 to the outside thereof through the second opening 30. During flossing operation, axial forces are applied to the segment of floss by the fingers through the ring portions. As the ring portions are pulled back and forth, force is applied in the opposite direction by the abutting end against the locking means. The locking means is restrained within the hollow elongate retaining means while the segment of floss freely extends therefrom. When the segment of floss has been used, the entire floss portion including the locking means is removed from the retaining means through the first opening and discarded. The ring portions are retained, and fitted with a fresh floss portion.

Figure 3:
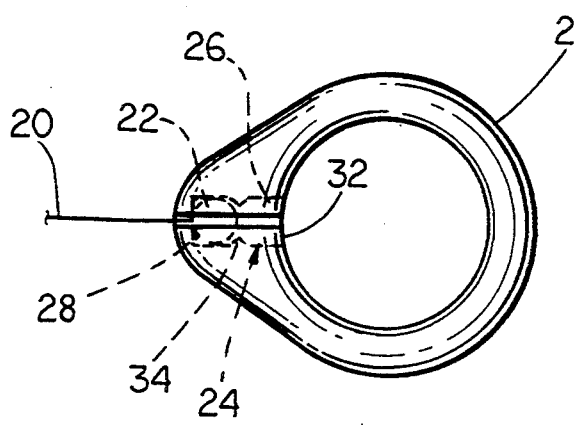
FIG. 3 is a top schematic view of an alternate embodiment of a ring portion of the invention comprising a snapping retaining means.

For added strength in retaining the locking means within the retaining means during flossing operation, the first opening of the retaining means may be elastically deformable and slightly smaller 34 than the outside diameter of the locking means so that the locking means can be snap-fitted into the retaining means, as shown in FIG. 3. This may also be achieved by forming the locking means of a resilient material. Alternatively, the first opening and/or hollow portion of the retaining means can be elastically deformable and sized to generally conform to the outside diameter of the locking means, so that the locking means can be forcibly retained within the retaining means.

A preferred embodiment of the invention is characterized by providing the retaining means wholly within the body of the ring portion, as shown in FIGS. 1 and 2, so that any protruding aspect of the retaining means is minimalized. This will result in a safer and more comfortable utilization of the device within the mouth. In addition, this arrangement allows for the point of attachment of the end of the floss segment to be closer to the finger, resulting in greater leverage and control of the floss segment.

It is contemplated that the invention encompasses a dental floss device comprising two ring portions and a floss portion held therebetween as described above. In addition, the invention comprises a dental floss device kit, in which two separate ring portions and at least one (and preferably a plurality of) separate floss portion are provided for easy construction of the dental floss device by the user. Furthermore, the invention resides in a ring portion for holding dental floss as described above, as well as in a dental floss having locking means on either end thereof.

What is claimed is:

1. A dental floss device comprising two finger sized ring portions and a floss portion held therebetween, each ring portion having a retaining means for holding an end of the floss portion, the floss portion comprising a segment of floss and a locking means at each end thereof for engagement with one of said retaining means, each locking means comprising an enlarged portion at a respective end of the segment of floss, wherein each retaining means engagingly receives a locking means, and at least one of the retaining means and the locking means being elastically deformable to snappingly retain the locking means within the retaining means.

2. A dental floss device comprising two finger sized ring portions and a floss portion held therebetween, each ring portion having a retaining means for holding an end of the floss portion, the floss portion comprising a segment of floss and a locking means at each end thereof for engagement with one of said retaining means, each retaining means engagingly receiving a locking means, each retaining means receiving a locking means through a first opening of the retaining means, the inside shape of the first opening generally conforming to the outside shape of the locking means to frictionally retain the locking means within the retaining means, wherein each retaining means has a second opening in communication with the first opening, which second opening is shaped to permit the passage therethrough of the segment of floss while preventing the passage therethrough of the locking means.

3. A dental floss device comprising two finger sized ring portions and a floss portion held therebetween, each ring portion having a retaining means for holding an end of the floss portion, the floss portion comprising a segment of floss and a locking means at each end thereof for engagement with each retaining means, the retaining means engagingly receiving a locking means, each retaining means receiving a locking means through a first opening of the retaining means, each retaining means having an abutting end communicating with the first opening for acting against a locking means in a direction toward the inside of the ring portion so as to thereby retain the locking means within the retaining means when forced is applied to the locking means via the segment of floss in a direction away from the inside of the ring portion, wherein each retaining means has a second opening in communication with the first opening, which second opening is shaped to permit the passage therethrough of the segment of floss while preventing the passage therethrough of the locking means.

4. The device of claim 3, wherein the retaining means is elongate, and the second opening runs from an edge of the first opening along the elongate retaining means towards the abutting end.

5. A dental floss device kit comprising two separate ring portions and a separate floss portion, wherein each ring portion has a retaining means and the floss portion comprises a segment of floss and a locking means at either end thereof for engagement with one of said retaining means, each locking means comprising an enlarged portion at a respective end of the segment of floss, wherein each retaining means engagingly receives a locking means, and at least one of the retaining means and the locking means being elastically deformable to snappingly retain the locking means within the retaining means.

6. A dental floss device kit comprising two separate ring portions and a separate floss portion, wherein each ring portion has a retaining means and the floss portion comprises a segment of floss and a locking means at each end thereof for engagement with one of said retaining means, each retaining means engagingly receiving a locking means, each retaining means receiving a locking means through a first opening of the retaining means, the inside shape of the first opening generally conforming to the outside shape of the locking means to frictionally retain the locking means within the retaining means, wherein each retaining means has a second opening in communication with the first opening, which second opening is shaped to permit the passage therethrough of the segment of floss while preventing the passage therethrough of the locking means.

7. The kit of claim 6, wherein the retaining means is elongate, and the second opening runs from an edge of the first opening along the elongate retaining means towards the abutting end.

8. A dental floss device kit comprising two separate ring portions and a separate floss portion, wherein each ring portion has a retaining means and the floss portion comprises a segment of floss and a locking means at each end thereof for engagement with one of said retaining means, each retaining means engagingly receiving a locking means, each retaining means receiving a locking means through a first opening of the retaining means, each retaining means having an abutting end communicating with the first opening for acting against a locking means in a direction toward the inside of the ring portion so as to thereby retain the locking means within the retaining means when force is applied to the locking means via the segment of floss in a direction away from the inside of the ring portion, wherein each retaining means has a second opening in communication with the first opening, which second opening is shaped to permit the passage therethrough of the segment of floss while preventing the passage therethrough of the locking means.

9. A dental floss holder for holding a segment of dental floss with an enlarged end comprising a locking means, the dental floss holder comprising a ring portion having a retaining means thereon for engagingly receiving the locking means, said retaining means adapted to receive the locking means through a first opening of the retaining means, the retaining means having an abutting end communicating with the first opening for acting against the locking means in a direction toward the inside of the ring portion so as to thereby retain the locking means within the retaining means when force is applied to the locking means via the segment of floss in a direction away from the inside of the ring portion, wherein the retaining means has a second opening in communication with the first opening, which second opening is shaped to permit the passage therethrough of the segment of floss while preventing the passage therethrough of the locking means.

10. The dental floss holder of claim 9, wherein the retaining means is elongate, and the second opening runs from an edge of the first opening along the elongate retaining means towards the abutting end.

11. A dental floss holder for holding a segment of dental floss with an enlarged end comprising a locking means, the dental floss holder comprising a ring portion having a retaining means thereon for engagingly receiving the locking means, said retaining means adapted to receive the locking means through a first opening of the retaining means, the inside shape of the first opening generally conforming to the outside shape of the locking means to frictionally retain the locking means within the retaining means, wherein the retaining means has a second opening in communication with the first opening, which second opening is shaped to permit the passage therethrough of the segment of floss while preventing the passage therethrough of the locking means.

* * * * *